United States Patent
Boyd

(10) Patent No.: US 9,442,072 B2
(45) Date of Patent: Sep. 13, 2016

(54) METHOD AND SYSTEM FOR RAMAN SPECTROSCOPY USING PLASMON HEATING

(71) Applicant: CALIFORNIA INSTITUTE OF TECHNOLOGY, Pasadena, CA (US)

(72) Inventor: David A. Boyd, La Cañada Flintridge, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 14/539,758

(22) Filed: Nov. 12, 2014

(65) Prior Publication Data
US 2015/0204793 A1   Jul. 23, 2015

Related U.S. Application Data

(60) Provisional application No. 61/902,950, filed on Nov. 12, 2013.

(51) Int. Cl.
G01N 21/65   (2006.01)
B82Y 15/00   (2011.01)

(52) U.S. Cl.
CPC ............. *G01N 21/658* (2013.01); *B82Y 15/00* (2013.01); *Y10S 977/932* (2013.01)

(58) Field of Classification Search
CPC .................................................. G01N 21/658
See application file for complete search history.

(56) References Cited

U.S. PATENT DOCUMENTS

| | | | |
|---|---|---|---|
| 6,095,982 A | 8/2000 | Richards-Kortum et al. | |
| 7,998,538 B2 | 8/2011 | Greengard et al. | |
| 2006/0061762 A1 | 3/2006 | Dwight et al. | |
| 2006/0275541 A1* | 12/2006 | Weimer | G01N 21/658 427/96.1 |
| 2008/0245430 A1* | 10/2008 | Adleman | B10L 3/50273 137/827 |
| 2010/0028908 A1* | 2/2010 | Stokes | G01N 21/658 435/7.4 |
| 2011/0026019 A1 | 2/2011 | Tyagi et al. | |
| 2011/0271738 A1* | 11/2011 | McGill | G01N 21/64 73/23.41 |
| 2012/0081703 A1* | 4/2012 | Moskovits | G01N 21/658 356/301 |
| 2013/0168789 A1 | 7/2013 | Lee et al. | |

FOREIGN PATENT DOCUMENTS

WO   2013-138313 A1   9/2013

OTHER PUBLICATIONS

Adleman, James R., et al. "Heterogenous catalysis mediated by plasmon heating." Nano letters 9.12 (2009): 4417-4423.*
International Search Report and Written Opinion, dated Jul. 24, 2015, for International Patent Application No. PCT/US2014/065277, with the International filing date of Nov. 11, 2014, 13 pages.

* cited by examiner

*Primary Examiner* — Kara E Geisel
*Assistant Examiner* — Shawn Decenzo
(74) *Attorney, Agent, or Firm* — Kilpatrick Townsend & Stockton LLP

(57) ABSTRACT

A method of identifying a sample includes placing the sample in proximity to a plurality of nanoparticles and irradiating the plurality of nanoparticles with laser radiation. A plasmon resonance process results in heating of the plurality of nanoparticles due to the laser irradiation. The method also includes transferring energy from the plurality of nanoparticles to the sample, obtaining a Raman spectrum associated with sample, and identifying the sample based on the Raman spectrum.

21 Claims, 8 Drawing Sheets

METHOD AND SYSTEM FOR RAMAN SPECTROSCOPY USING PLASMON HEATING

CROSS-REFERENCES TO RELATED APPLICATIONS

This application claims priority to U.S. Provisional Patent Application No. 61/902,950, filed on Nov. 12, 2013, entitled "Method of Localized Heating for Raman Spectroscopy," the disclosures of which are hereby incorporated by reference in their entirety for all purposes.

STATEMENT AS TO RIGHTS TO INVENTIONS MADE UNDER FEDERALLY SPONSORED RESEARCH OR DEVELOPMENT

This invention was made with government support under W911SR-12-C-0003 awarded by the Army. The government has certain rights in the invention.

BACKGROUND OF THE INVENTION

Raman microscopy has been used to investigate molecular structure of various types of matter and materials. This approach involves locating an area of interest with a microscope and then probing the area of interest with a laser. Energy changes in the scattered laser light give rise to a Raman spectrum that can be used to identify or characterize the material of interest.

Despite the progress made in Raman microscopy, there is a need in the art for improved methods and systems related to performing Raman microscopy.

SUMMARY OF THE INVENTION

The present invention relates generally to systems and methods for material characterization. More specifically, embodiments of the present invention relate to Raman microscopy. In a particular embodiment, Raman microscopy is performed for samples that are heated by a plasmon resonance process.

As described herein, embodiments of the present invention utilize plasmon heating to provide a compact, inexpensive, and rapid method for localized sample heating while simultaneously or concurrently acquiring a Raman spectrum. System complexity is reduced since the same beam that is used for Raman spectroscopy is used in relation to the localized heating. Because of the localized nature of the plasmon heating process, areas to be investigated can be located in close proximity to each other, enabling independent and rapid characterization of multiple proximal areas.

Embodiments of the present invention are useful in identifying samples, for example, energetic compounds that are unstable in the sense that they tend to decompose upon heating. Exemplary compounds that are suitable for use with embodiments of the present invention include explosives, polymers, energetic materials, volatile materials, minerals, and the like. Conventional approaches that utilize a furnace to heat the sample, result in heating of the entire sample, which prevents local characterization of specific portions of the sample. In contrast with these conventional techniques, embodiments of the present invention are able to measure small sample sizes, including grains on the order of microns in dimension, quickly and accurately.

According to an embodiment of the present invention, a method of identifying a sample is provided. The method includes placing the sample in proximity to a plurality of nanoparticles and irradiating the plurality of nanoparticles with laser radiation. The method also includes transferring thermal energy from the plurality of nanoparticles to the sample to heat the sample and obtaining a Raman spectrum associated with heated sample. The method further includes identifying the sample based on the Raman spectrum.

According to another embodiment of the present invention, a method of characterizing a sample is provided. The method includes placing the sample in contact with a plurality of nanoparticles, irradiating the plurality of nanoparticles with electromagnetic radiation at a first fluence, and increasing a temperature of the plurality of nanoparticles from an influence of the electromagnetic radiation. The method also includes transferring energy from the plurality of nanoparticles to the sample and collecting a first Raman spectrum from the sample. The method further includes irradiating the plurality of nanoparticles with electromagnetic radiation at a second fluence greater than the first fluence and increasing the temperature of the plurality of nanoparticles from an influence of the electromagnetic radiation at the second fluence. Additionally, the method includes transferring additional energy from the plurality of nanoparticles to the sample and collecting a second Raman spectrum from the sample. Furthermore, the method includes determining characteristics of the sample based on the first Raman spectrum and the second Raman spectrum.

According to a specific embodiment of the present invention, a Raman microscopy system is provided. The Raman microscopy system includes a laser and an optical system optically coupled to the laser. The Raman microscopy system also includes a cover slip (e.g., a microscope cover slip) including a layer of nanoparticles and a sample region in the vicinity of the layer of nanoparticles and operable to receive a sample. The Raman microscopy system further includes a spectral detector operable to receive Raman spectra scattered from the sample.

Numerous benefits are achieved by way of the present invention over conventional techniques. For example, embodiments of the present invention provide techniques that utilize a single laser source for both exciting Raman scattering for Raman spectroscopy and heating of the nanoparticles through a plasmon resonance process. Additionally, embodiments of the present invention provide methods and systems that are useful in detecting materials utilized in explosives, volatile compounds, and the like. These and other embodiments of the invention along with many of its advantages and features are described in more detail in conjunction with the text below and attached figures.

DETAILED DESCRIPTION OF SPECIFIC EMBODIMENTS

Figure 1A:
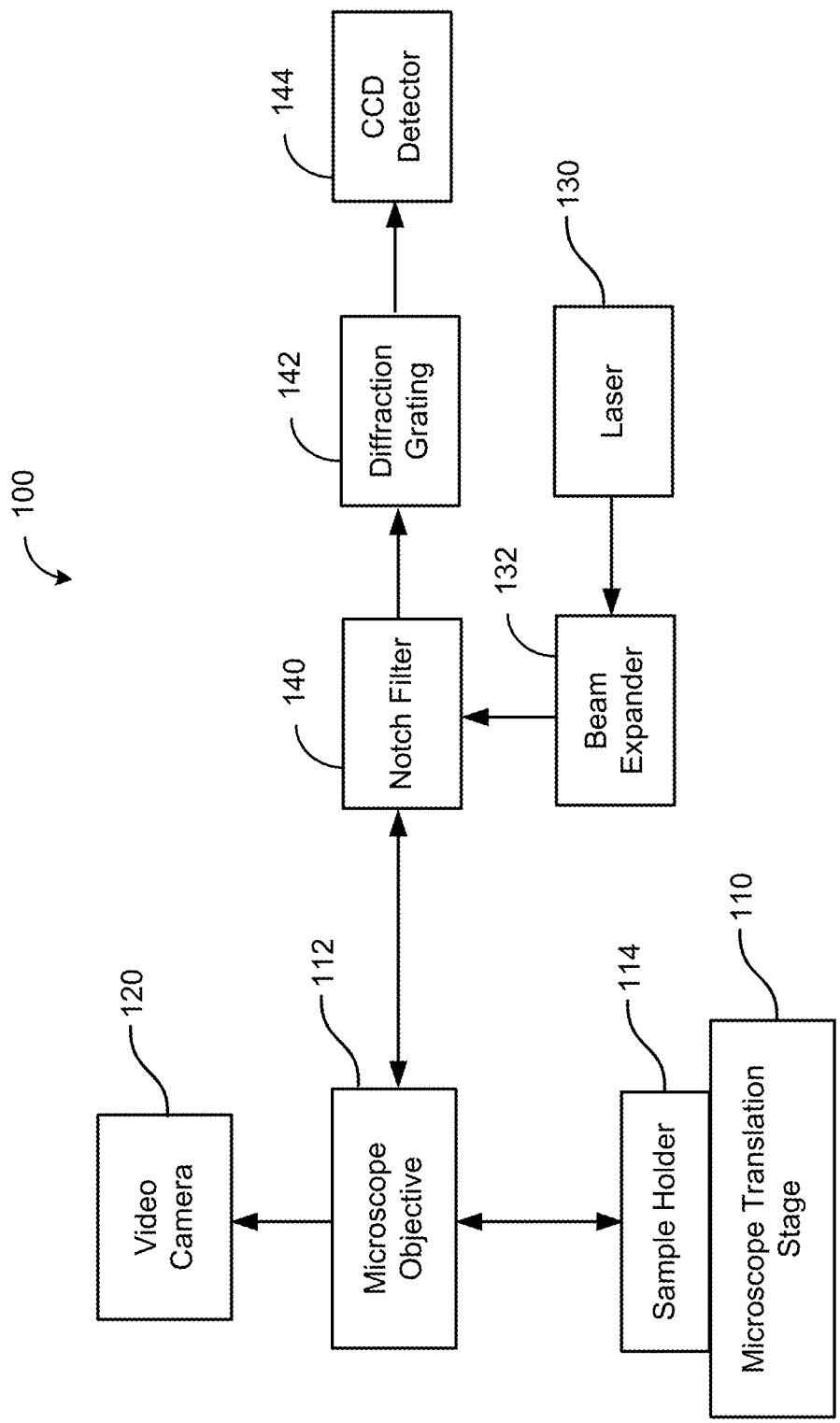
FIG. 1A is a simplified schematic diagram of a Raman microscopy system using plasmon heating according to an embodiment of the present invention.

FIG. 1A is a simplified schematic diagram of a Raman microscopy system using plasmon heating according to an embodiment of the present invention. The Raman microscopy system 100 includes a laser source that includes laser 130 and beam expander 132. Light from the laser source is directed through notch filter 140, for example, a holographic notch filter, and is focused through microscope objective 112 onto a sample positioned on the sample holder 114. The sample holder is supported on microscope translation state 110 that can be operated under computer control, manual control, or the like. Positioning of the incident irradiation laser light on the sample can be controlled using the video camera 120 and the microscope translation stage.

Light scattered from the sample is collected using microscope objective 112 and passes through the notch filter 140, is dispersed by the diffraction grating 142, and measured at CCD detector 144. By rotating the diffraction grating, or other spectrally selective technique, the spectrum of the scattered light can be measured.

Figure 1B:
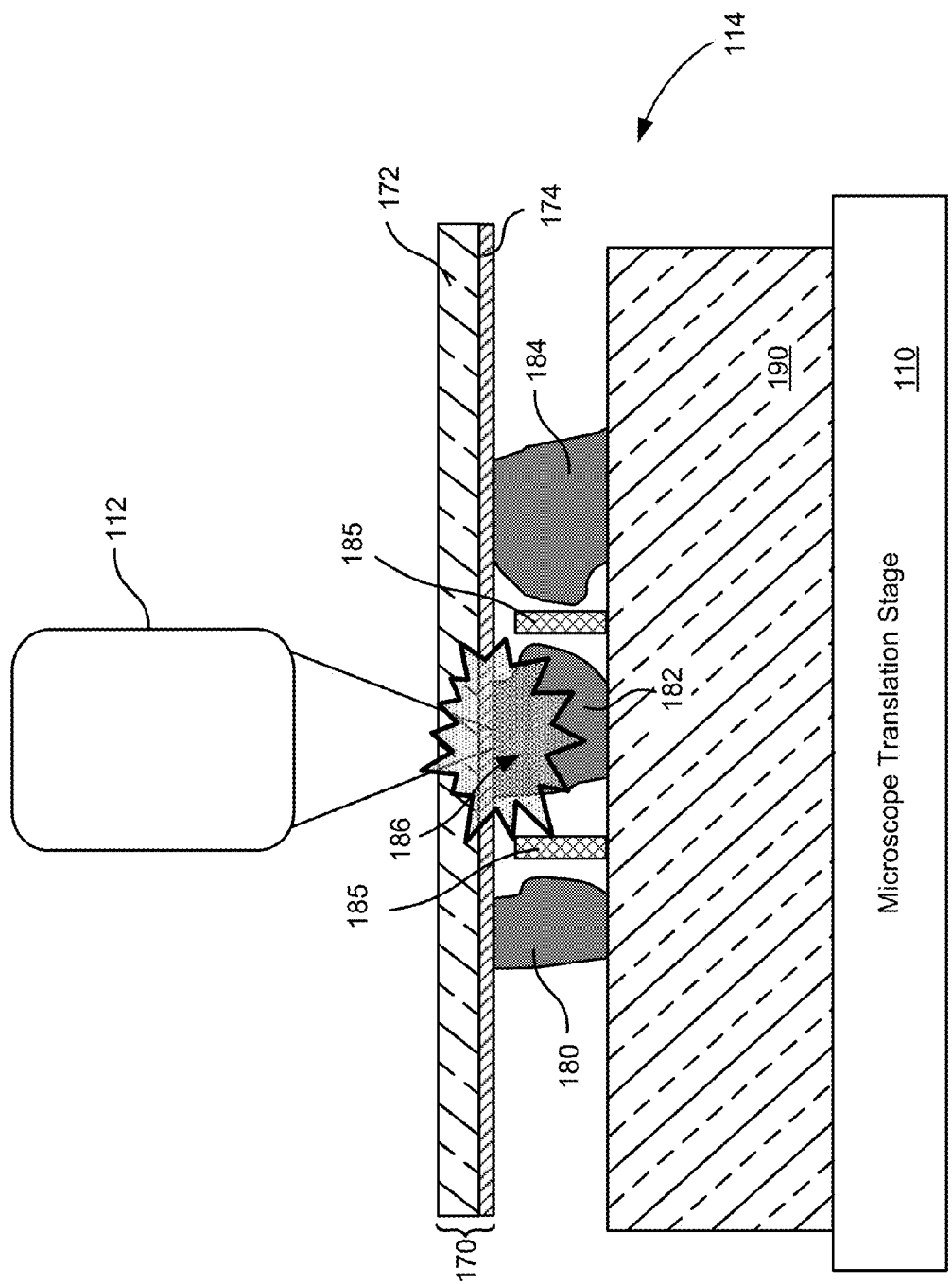
FIG. 1B is a simplified schematic diagram of elements of the Raman microscopy system illustrated in FIG. 1A.

FIG. 1B is a simplified schematic diagram of elements of the Raman microscopy system illustrated in FIG. 1A. In particular, the microscope objective 112 and the sample holder 114 are described in additional detail in relation to this figure. Referring to FIG. 1B, a cover slip 170, for example, a microscope cover slip, which can also be referred to as a compound substrate, includes a substrate material 172 and a layer of nanoparticles 174. In some embodiments, the cover slip 170 is fabricated from glass although other materials that are substantially transparent to the incident radiation and the scattered radiation and have sufficient mechanical rigidity and chemical stability can be utilized. In some exemplary implementations, the substrate material 172 can be fabricated from quartz, glass, combinations thereof, or the like. The layer of nanoparticles 174 is deposited on or laminated to the substrate material in the illustrated embodiment although this is not required by embodiments of the present invention. One of ordinary skill in the art would recognize many variations, modifications, and alternatives.

The layer of nanoparticles 174 are provided on a surface of the substrate material 172. In the illustrated implementation, the layer of nanoparticles includes a plurality of metallic structures having nanoscale structural features are formed in contact with the substrate material. In some implementations, the nanoparticles can be formed as generally spherical or hemispherical particles and can have a radius from about 0.5 nm to about 500 nm, for example, from about 1 nm to about 100 nm, more particularly, a few tens of nanometers. The particles can be dispersed in a random or predetermined pattern depending on the particular implementation. Metal nanoparticles with an optical resonance, e.g., gold, are utilized in some embodiments although other nanoparticles are included within the scope of the present invention.

Adjacent the cover slip 170, one or more samples 180, 182, and 184 are positioned between the cover slip and a substrate 190, which can be a glass slide or other suitable substrate material. In the embodiment illustrated in FIG. 1B, three discrete samples are illustrated, but this is not required by the present invention. In some embodiments, the substrate 190 includes a grid of barriers 185 that divide the samples into discrete test regions between the barriers. Using such a grid of barriers, different samples can be placed in the test regions, multiple samples of a same material can be placed in the test regions, or the like. The arrangement of the layer of nanoparticles and the samples illustrated in FIG. 1B can be referred to as a top heating arrangement.

As described herein, laser radiation is absorbed by the nanoparticles through a plasmon resonance process. The plasmon resonance absorption results in an increase in temperature of the nanoparticles to provide a localized heating source. Thermal energy from this localized source is transferred to the sample at a location adjacent the laser radiation, thereby locally heating the sample. Referring to FIG. 1B, the incident laser radiation is focused in focus region 186, which includes a portion of the nanoparticles 174 and a portion of the sample 182. The position of the samples under the cover slip provides good optical access to the nanoparticles since the nanoparticles are optically upstream of the samples and receive the laser radiation before the laser radiation impinges on the samples. The presence of the nanoparticles results in absorption of a portion of the laser radiation and heating of the nanoparticles through the plasmon resonance process. The plasma resonance process proceeds to heat sample 182 on a time scale on the order of seconds, which is orders of magnitude faster than heating in a furnace.

The laser radiation is focused using microscope objective 112 to a small spot size in focus region 186. In exemplary embodiments, focus region 186 characterized by a spot size, for example, a spot size on the order or microns (i.e., 100 μm, 50 μm, 25 μm, 10 μm, or less) in area. Because the plasmon resonance process depends on the incident radiation, the heat generated through the plasmon resonance process is highly localized (e.g., on the order of microns in dimension), enabling the characterization of micron-sized samples. The microscope translation stage 110 can then be used to position sample 180 or sample 184 in the focus region so that these samples can be characterized.

In conventional Raman microscopy systems, heating of the sample is performed using a furnace. There are several drawbacks to the this approach, including 1) the large size of the system relative to the sample, 2) these systems are costly, and 3) heating of the sample in a furnace is slow relative to the measurement time. Furthermore, the heating cannot be localized to portions of the sample since the entire sample is heated rather than just an area of interest.

Referring to FIG. 1B, the cover slip 170 is pressed or urged toward the substrate 190 during mounting of the samples in the top heating arrangement. As a result, the samples 180, 182, and 184 are placed in close proximity to the nanoparticles 174. In some embodiments, the substrate 190 is positioned in order to provide physical contact between the nanoparticles and the sample. The physical contact results in high thermal conductivity between the nanoparticles and the sample. In other embodiments, a thermal conductor, such as a fluid or gel is placed between the nanoparticles and the sample (e.g., making physical contact with the nanoparticles and the sample) to transfer energy from the nanoparticles to the sample.

As illustrated in FIG. 1B, the nanoparticles 174 are attached to the substrate material 172. Consequently, when the nanoparticles heat up to high temperatures as a result of the plasmon resonance process, the conductive heat transfer is limited in the lateral direction, resulting in heat transfer to the sample. Because the heating of the sample results from heating of the nanoparticles, low power lasers (e.g., 1 mw to 100 mW lasers) can be utilized in embodiments of the present invention while still transferring sufficient energy to the sample to increase the temperature of the sample to hundreds of degrees Celsius (e.g., 800° C.) and produce ignition, decomposition, detonation, and/or other phase changes.

The electromagnetic radiation utilized in some implementations is in the form of a laser beam provided by a laser source. Various laser sources, optical amplifiers, optical frequency conversion devices, and lasers can be utilized in accordance with the present invention. The electromagnetic radiation, for example, can be ultraviolet, visible, or infrared radiation or any combination thereof.

According to embodiments of the present invention, the electromagnetic radiation is at or near a photon-electron resonant frequency and collective oscillations or a resonance of the surface electrons is associated with a plasmon resonance. As the size of a structures decreases, there is an increase in the surface-to-volume ratio, which is proportional to 1/R, where R is the radius of the particle. Nanoparticles, in particular, have high surface-to-volume ratios so that there are a larger number of surface electrons relative to bulk electrons. The surface electrons are delocalized and can be excited with visible light at or near the plasmon resonant frequency of the electrons. It is generally believed that this accounts for the efficient heating of nanoparticles by electromagnetic radiation at the plasmon resonance frequency. The optimal absorption frequency can depend both on the shape of individual nanoparticles as well as the geometric arrangement of a collection of nanoparticles (e.g., on a surface). Recent experimental evidence suggests that the plasmon resonance phenomenon can occur on very fast time scales. Additional description related to plasmon resonances in nanoparticles is provided in U.S. Pat. No. 7,998,538, entitled "Electrochemical Control of Chemical Catalysis," the disclosure of which is hereby incorporated by reference in its entirety for all purposes.

Raman scattering from the sample as it is heated is collected through the microscope objective 112 and other elements illustrated in FIG. 1A, enabling the collection of the Raman spectrum as a function of sample temperature. Because the Raman spectra change as a function of sample temperature for many materials, material characterization is possible. This includes analysis of component materials making up the sample. It should be noted that since the heat transfer is limited in the lateral direction, the Raman signal is dominated by the sample or portions of the sample that are in thermal contact with the nanoparticles in the focus region.

Figure 1C:
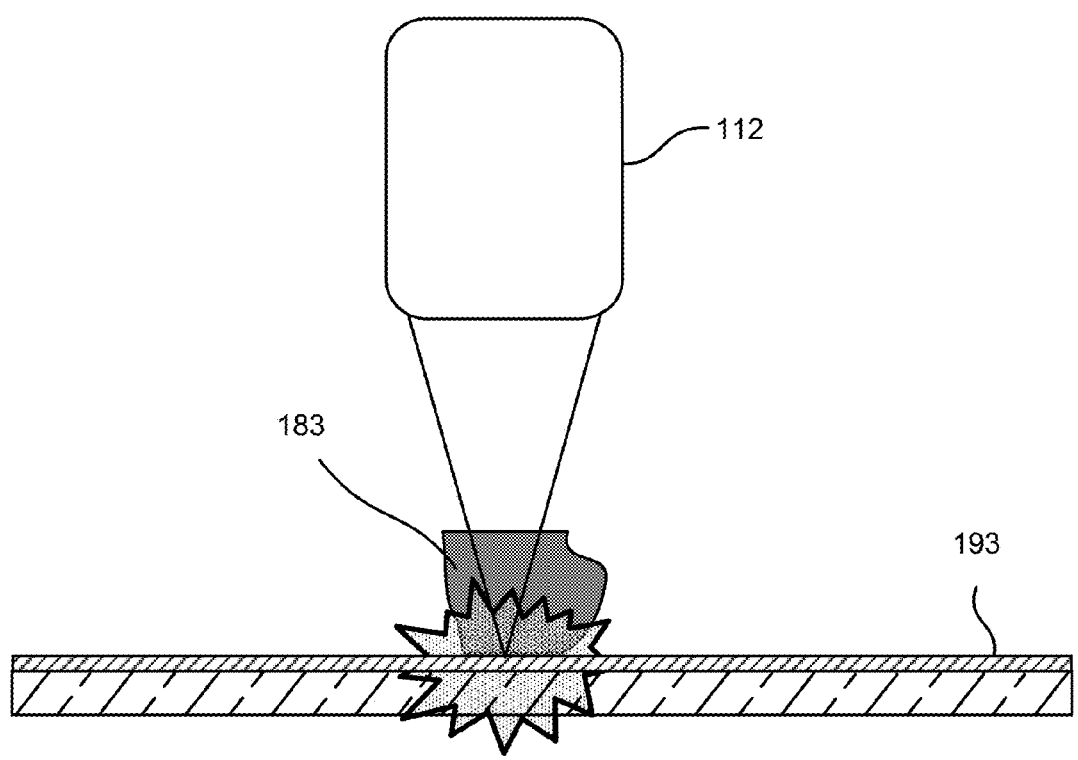
FIG. 1C is a simplified schematic diagram of elements of a bottom heating Raman spectroscopy system according to an embodiment of the present invention.

Using the top heating arrangement illustrated in FIG. 1B, the cover slip 170 prevents vapors produced during heating of the sample from escaping into the atmosphere. The top heating arrangement illustrated in FIG. 1B is superior to implementations in which the sample is placed between the microscope objective and the layer of nanoparticles, which can be referred to as a bottom heating arrangement as illustrated in FIG. 1C. The sample 183 is positioned on layer of nanoparticles 193 and heat from the nanoparticles is transferred to the sample from the bottom. The sample rests on the layer of nanoparticles and lacks the mechanical pressure associated with the position between the cover slip and the substrate illustrated in FIG. 1B. Accordingly, the thermal contact between the sample and the nanoparticles may not be sufficient to provide consistent and uniform heating. The laser passes through and is scatted by the sample before impinging on the nanoparticles, which reduces intensity at the focus region. Additionally, the Raman signal is biased toward portions of the sample that face away from the nanoparticles, increasing the noise level. In this implementation, gases that evaporate from the sample during testing, particular volatile compounds, are able to flow away from the focus region, which contrasts with the prevention of such escaping in the implementation illustrated in FIG. 1B in which the volatile species are retained within the vicinity of the sample by the cover slip. It should be noted that embodiments of the present invention are also applicable to materials that melt or liquefy as a result of the plasmon heating.

Figure 2:
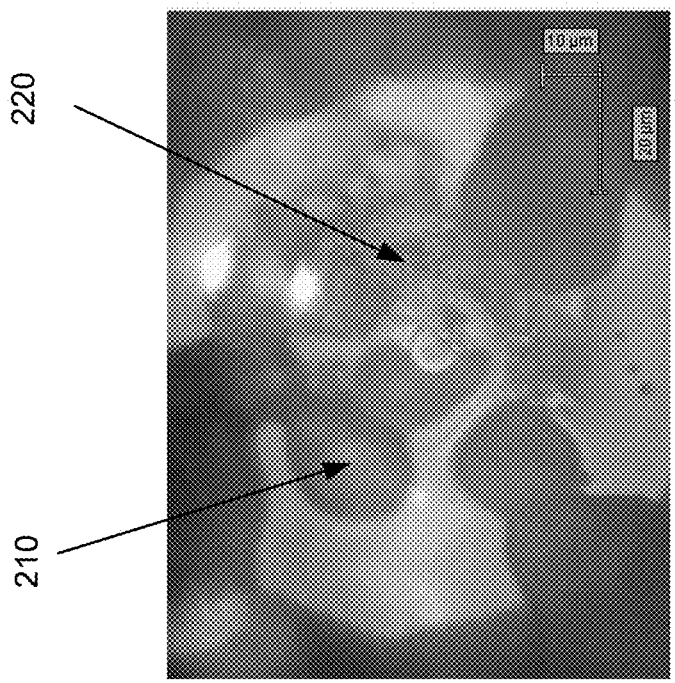
FIG. 2 is a picture illustrating a first sample before and after decomposition during Raman spectroscopy using plasmon heating.

FIG. 2 is a picture illustrating a first sample before and after decomposition during Raman spectroscopy using plasmon heating. Referring to FIG. 2, a photograph is providing illustrating destructive testing of a portion of a sample, in this case, an energetic material, using Raman spectroscopy with sample heating through a plasmon resonance process according to an embodiment of the present invention. In FIG. 2, an undisturbed portion 210 of a grain of an ammonium-nitrate fuel oil (ANFO) material is illustrated. Portion 210 would result in a Raman spectrum associated with the undisturbed material. Another portion 220 of the grain has been detonated after heating using plasmon resonance. The material properties have changed along with a change in the Raman spectrum.

Figure 3:
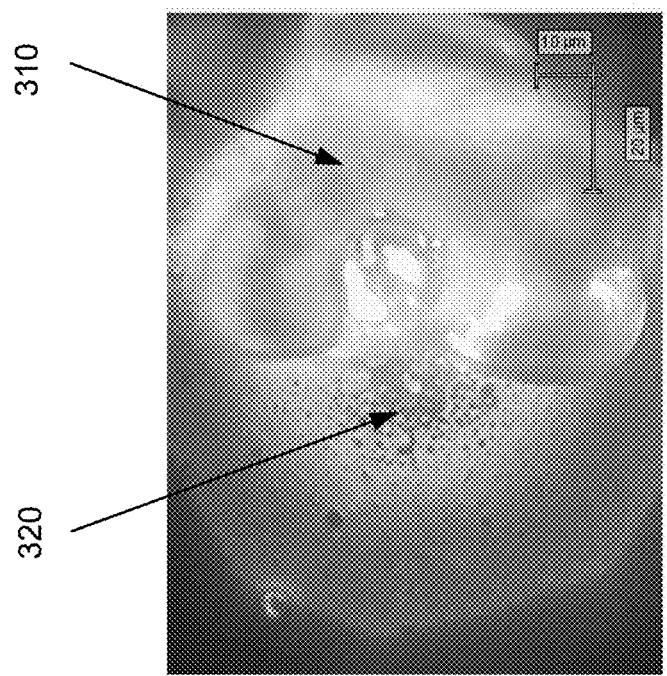
FIG. 3 is a picture illustrating a second sample before and after decomposition during Raman spectroscopy using plasmon heating.

FIG. 3 is a picture illustrating a second sample before and after decomposition during Raman spectroscopy using plasmon heating. In this figure, the ANFO is undisturbed in portion 310 and has been detonated in portion 320. In practice, the decomposed portion is initially in the undisturbed state. As the laser power is increased, either through increases in the repetition rate of the laser source, increases in the amplitude of the laser output, decreases in the spot size, or the like, the temperature of the nanoparticles increases as a result of increases in the plasmon resonance process. Raman spectra can be obtained as the laser power is increased. This process of increasing the laser power to a series of power levels and collection of Raman spectra can be repeated until the sample is detonated, ignited, decomposes, or undergoes another type of phase change as the temperature increases. The Raman spectra can be analyzed as a function of laser power/sample temperature to characterize the sample.

In the examples illustrated in FIGS. 2 and 3, not only has a phase transformation occurred for the material as a result of the plasmon heating, but the Raman signature changes as well as discussed in relation to FIG. 4 below.

Figure 4:
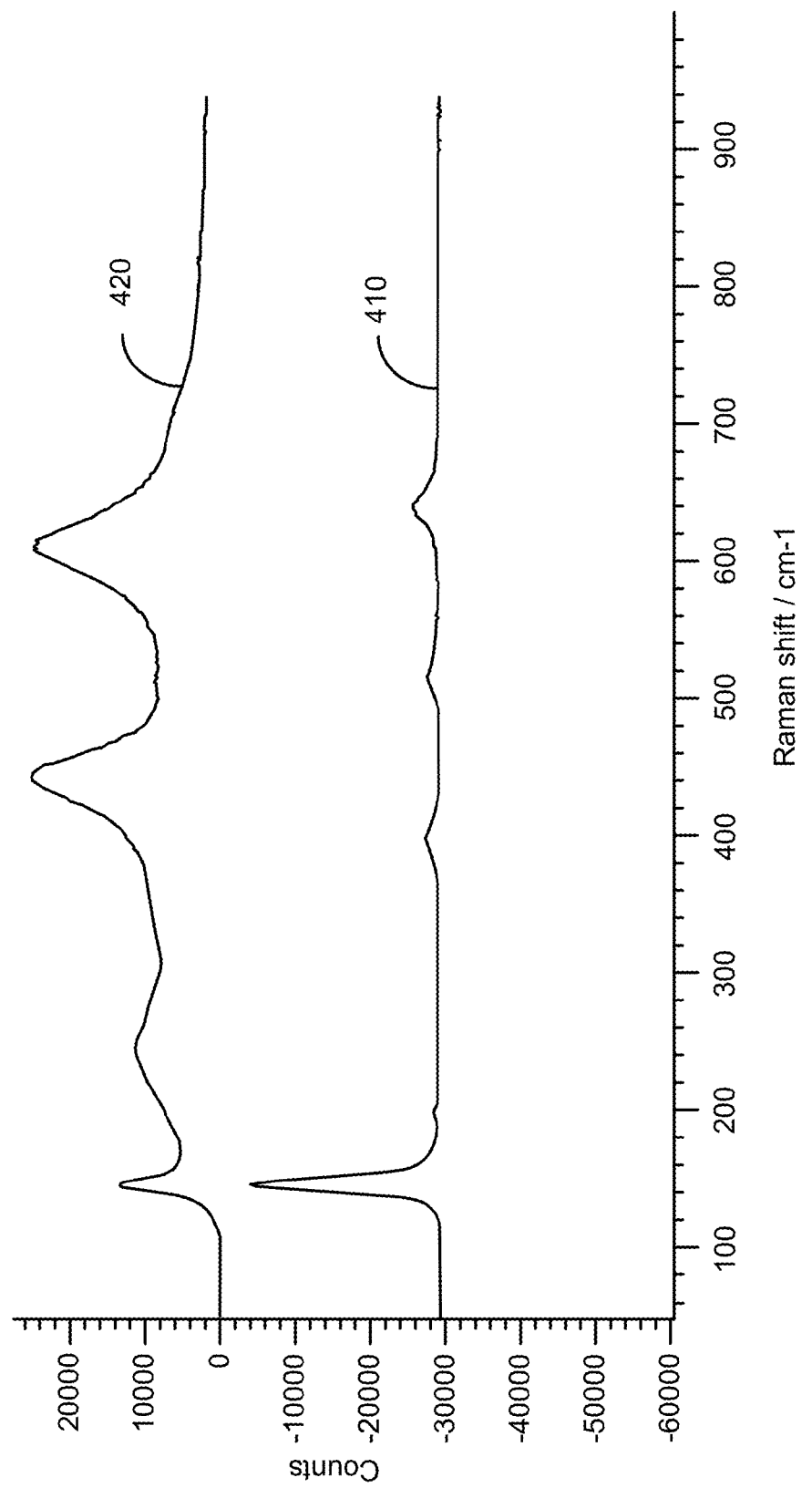
FIG. 4 is a simplified plot illustrating Raman spectra of a sample undergoing a phase transformation according to an embodiment of the present invention.

FIG. 4 is a simplified plot illustrating Raman spectra of a sample undergoing a phase transformation according to an embodiment of the present invention. As illustrated in FIG. 4, plasmon heating of the sample induces a phase transformation that can be characterized using Raman spectroscopy. Curve 410 in the figure is the Raman spectrum obtained at room temperature for a sample of titania (i.e., titanium dioxide, $TiO_2$). Titania has two phases or polymorphs: anatase and rutile. At room temperature, titania is in the anatase phase and is characterized by a single significant peak at ~150 cm$^{-1}$. It should be noted that the curve 410 is offset by 3000 counts in order to present both curves in the same plot. Raman spectroscopy can provide materials identification and characterization through analysis of the positions of the peak(s) or other features in the spectrum, the amplitudes of the peak(s) or other features in the spectrum, and the widths of the peak(s) or other features in the spectrum. In FIG. 4, curve 410 is obtained at a laser fluence such that heating of the nanoparticles, and the sample as a result, does not occur, but a Raman spectrum is measureable.

After irradiation of the nanoparticles using the laser, the titania sample is heated to a temperature in the range of 500° C. to 1,000° C., resulting in a phase transformation from the anatase phase to the rutile phase. As illustrated by curve 420, the single peak at ~150 cm$^{-1}$ characteristic of the anatase phase has been reduced in amplitude and the amplitude of the peaks at ~425 cm$^{-1}$ and ~600 cm$^{-1}$ have significantly increased with respect to the amplitude of the peak at ~150 cm$^{-1}$ as a result of the conversion to the rutile phase. Accordingly, the phase transformation that the titania undergoes is readily characterized using the Raman spectroscopy system described herein and illustrated by curves 410 and 420 associated with differing phases.

Although only two states of the material, which can be associated with two fluences, are illustrated in FIGS. 2, 3, and 4, embodiments of the present invention can obtain a plurality of Raman spectra as the laser fluence is increased and the temperature of the sample increases. The variation of characteristics of the Raman spectra as a function of temperature can then be utilized to characterize the material or materials present in the sample.

Figure 5:
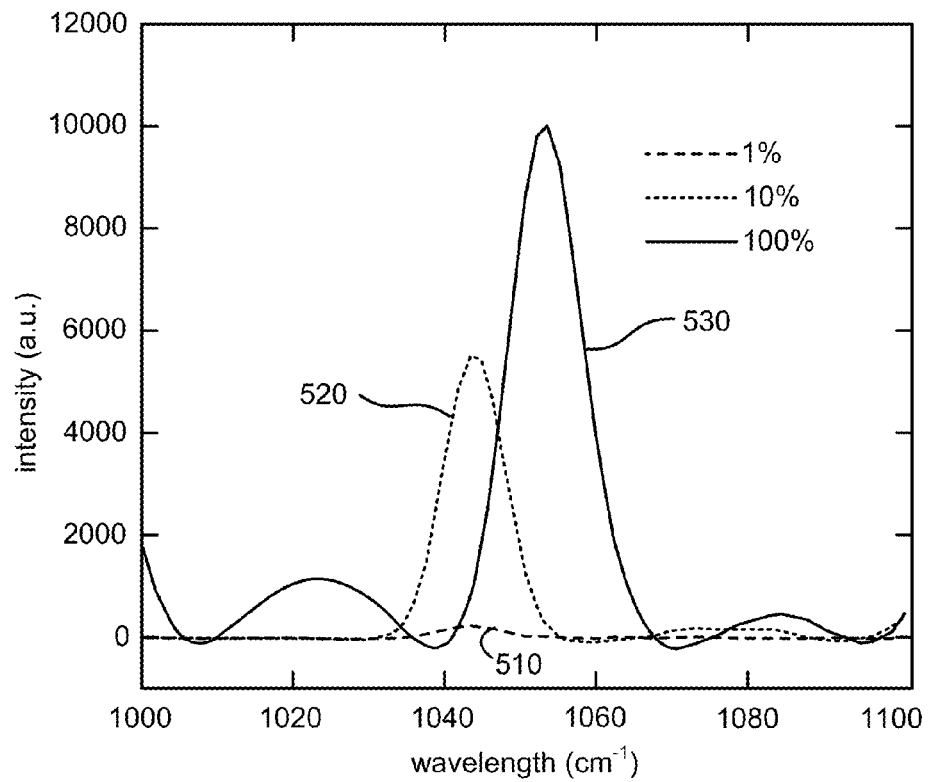
FIG. 5 is a simplified plot illustrating Raman spectra of a sample at increasing laser fluence according to an embodiment of the present invention.

FIG. 5 is a simplified plot illustrating Raman spectra of a sample at increasing laser fluence according to an embodiment of the present invention. In FIG. 5, the Raman spectra for laser intensity at 1% of the full intensity 510, 10% of the full intensity 520, and 100% of the full intensity 530 are illustrated. At the lowest intensity, and the corresponding low level of heating through the plasmon resonance, the spectrum 510 is substantially flat since the signal is small at low intensity. As the intensity is increased and the sample is heated to an initial temperature as a result of the plasmon resonance heating, the spectrum 520 exhibits a peak at ~1040 cm$^{-1}$ associated with about 6,000 counts (arbitrary units).

At the full intensity and a higher temperature, the spectrum 530 increases in amplitude, reaching about 10,000 counts as would be expected due to the higher intensity. However, importantly, the peak of the spectrum shifts from ~1040 cm$^{-1}$ to 18 1055 cm$^{-1}$. The spectral shift in response to the heating of the sample is a useful diagnostic that can be used to determine sample identity, sample composition, other material characteristics, or the like.

Figure 6:
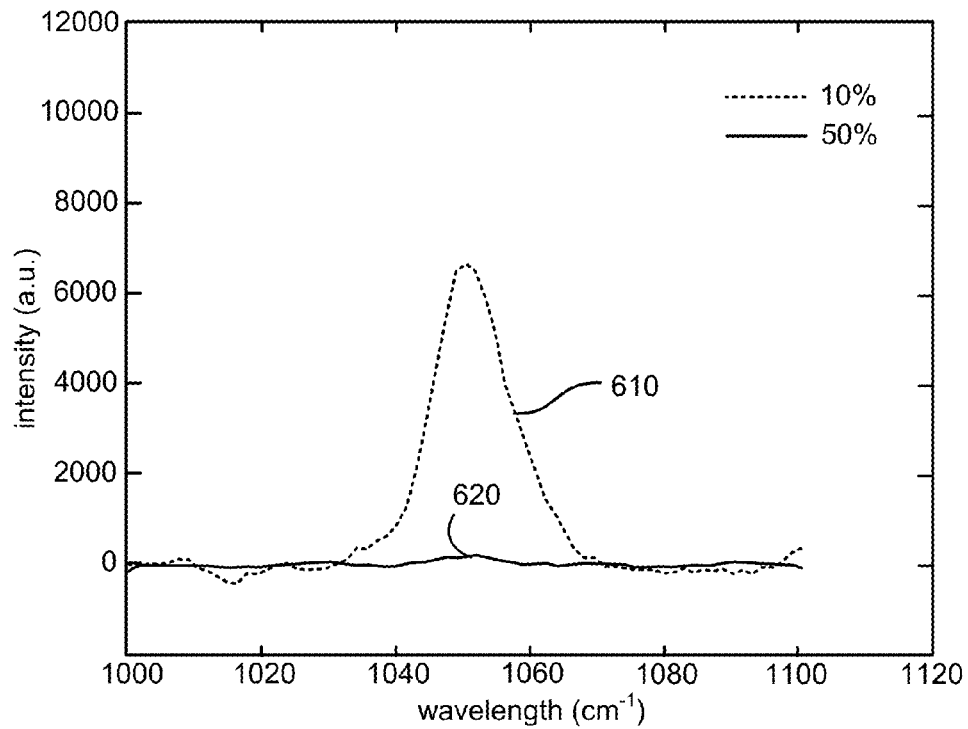
FIG. 6 is a simplified plot illustrating Raman spectra of a sample during a vaporization process according to an embodiment of the present invention.

FIG. 6 is a simplified plot illustrating Raman spectra of a sample during a vaporization process according to an embodiment of the present invention. Sharing some similarities with the plot illustrated in FIG. 5, the Raman spectra for laser intensity at 10% of the full intensity 610 and 50% of the full intensity 620 are illustrated. The spectrum 610 at lower intensity includes a peak at ~1055 cm$^{-1}$. As the temperature increases, the sample is heated and at or before reaching 50% of the full intensity, the sample detonates, resulting in vaporization of some or all of the sample. At these high fluences, the heating of the nanoparticles and the resulting energy transfer to the sample results in the sample being heated to a point of melting and then evaporation. For energetic compounds, the sample changes phase rapidly, effectively exploding. In some embodiments, the vaporization of portions of the sample results in volatile compounds in the sample, which at low intensities produce a Raman signal, being vaporized and thereby producing no Raman signal at the original wavelength. As the Raman signal disappears as the temperature is increased, useful diagnostic information is available to the user.

Figure 7:
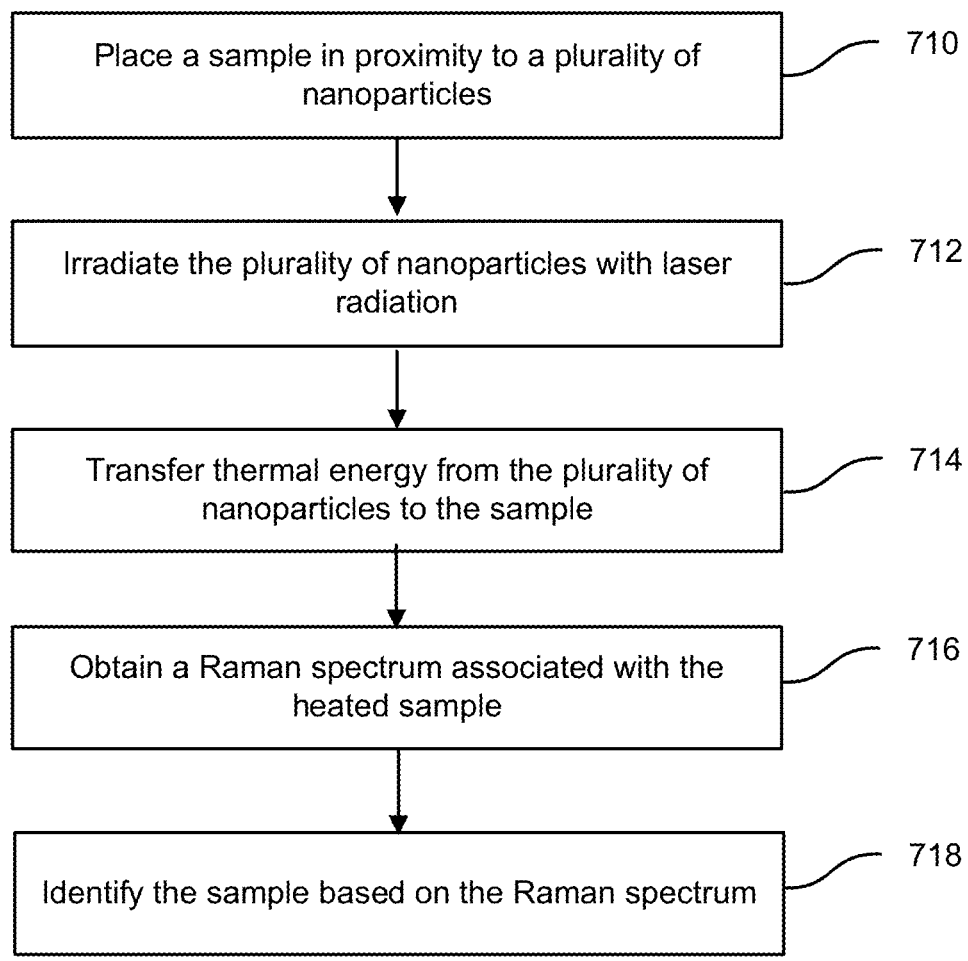
FIG. 7 is a simplified flowchart illustrating a method of identifying a sample according to an embodiment of the present invention.

FIG. 7 is a simplified flowchart illustrating a method of identifying a sample according to an embodiment of the present invention. The method 700 includes placing the sample in proximity to a plurality of nanoparticles (710). In some embodiments, the sample is supported on a substrate and the plurality of nanoparticles are formed as a layer and attached to a cover slip that is pressed against the sample on the substrate, with the layer of nanoparticles facing the sample. Physical contact between the sample and the plurality of nanoparticles can be utilized to increase the thermal conductivity between the plurality of nanoparticles and the sample. In other embodiments, a thermal conductor is placed between the sample the plurality of nanoparticles. One of ordinary skill in the art would recognize many variations, modifications, and alternatives.

The method also includes irradiating the plurality of nanoparticles with laser radiation (712) and transferring thermal energy from the plurality of nanoparticles to the sample (714). The transfer of thermal energy results in heating of the sample. The absorption of the laser radiation by the plurality of nanoparticles utilizes a plasmon resonance process that provides rapid and localized heating of the nanoparticles and the sample as a result. Depending on the fluence of the laser radiation, a phase change in the sample can be associated with the energy transfer as the sample is heated. As illustrated in FIGS. 2 and 3, evaporation, liquefaction, or decomposition of the sample can occur as the sample is rapidly heated.

The method further includes obtaining a Raman spectrum associated with heated sample (716) and identifying the sample based on the Raman spectrum (718). The Raman spectrum associated with a sample can be characterized using one of several methods and metrics associated with the Raman spectrum can be utilized to identify the sample. As an example, the peak wavelengths, width, and amplitudes can be used during the sample identification process. The changes of the spectra with plasmon heating can be used to characterize and identify the sample composition. In some embodiments of the present invention, the same laser is used to irradiate the nanoparticles, resulting in heating of the sample, and to obtain the Raman spectrum. In other embodiments, separate lasers are utilized to irradiate the nanoparticles and to produce the Raman spectra. One of ordinary skill in the art would recognize many variations, modifications, and alternatives.

It should be appreciated that the specific steps illustrated in FIG. 7 provide a particular method of identifying a sample according to an embodiment of the present invention. Other sequences of steps may also be performed according to alternative embodiments. For example, alternative embodiments of the present invention may perform the steps outlined above in a different order. Moreover, the individual steps illustrated in FIG. 7 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 8:
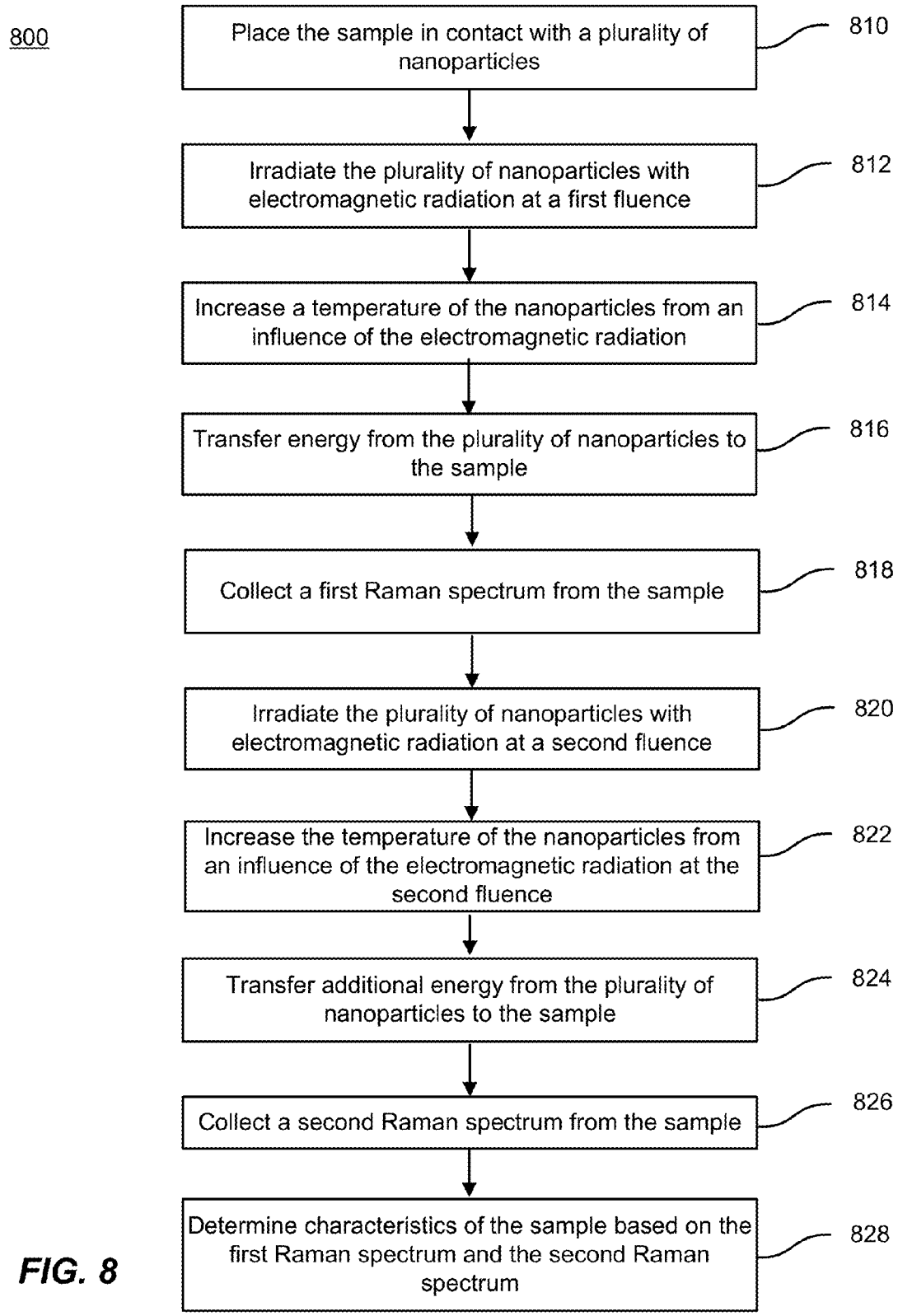
FIG. 8 is a simplified flowchart illustrating a method of characterizing a sample according to an embodiment of the present invention.

FIG. 8 is a simplified flowchart illustrating a method of characterizing a sample according to an embodiment of the present invention. The method 800 includes placing the sample in contact with a plurality of nanoparticles (810) and irradiating the plurality of nanoparticles with electromagnetic radiation (e.g., laser radiation) at a first fluence (812). Placing the sample in contact with the plurality of nanoparticles can include providing a substrate, providing a cover slip comprising the plurality of nanoparticles, positioning the sample between the substrate and the cover slip. In the top heating arrangement described herein, the plurality of nanoparticles are disposed on a surface of the cover slip and the surface of the cover slip faces the sample such that the incident radiation impinges on the plurality of nanoparticles before or concurrently with the sample.

The method also includes increasing a temperature of the plurality of nanoparticles from an influence of the electromagnetic radiation (814), transferring energy from the plurality of nanoparticles to the sample (816), and collecting a first Raman spectrum from the sample (818). As the plurality of nanoparticles are heated through a plasmon resonance process, the heat is transferred to the sample and the sample is heated. The first Raman spectrum is associated with the sample at a first temperature and is characterized by metrics associated with the sample at the first temperature. In some embodiments, the first temperature is room temperature when the fluence is low (e.g., 1% of the maximum fluence) and the Raman spectrum can provide a baseline for comparison with subsequent spectra.

The method further includes irradiating the plurality of nanoparticles with electromagnetic radiation at a second fluence greater than the first fluence (820), increasing the temperature of the plurality of nanoparticles from an influence of the electromagnetic radiation at the second fluence (822), and transferring additional energy from the plurality of nanoparticles to the sample (824). Additionally, the method includes collecting a second Raman spectrum from the sample (826) and determining characteristics of the sample based on the first Raman spectrum and the second Raman spectrum (828). The second Raman spectrum is obtained with the sample at a second temperature higher than the first temperature and the temperature differential produces a set of differing spectra that can be utilized to characterize the material(s) making up the sample.

In some embodiments, the first Raman spectrum is associated with a first phase of the sample and the second Raman spectrum is associated with a second phase of the sample, for example, evaporation of the sample.

It should be appreciated that the specific steps illustrated in FIG. 8 provide a particular method of characterizing a sample according to an embodiment of the present invention. Other sequences of steps may also be performed according to alternative embodiments. For example, alternative embodiments of the present invention may perform the steps outlined above in a different order. Moreover, the individual steps illustrated in FIG. 8 may include multiple sub-steps that may be performed in various sequences as appropriate to the individual step. Furthermore, additional steps may be added or removed depending on the particular applications. One of ordinary skill in the art would recognize many variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:
1. A method of identifying a sample, the method comprising:
   placing the sample in proximity to a plurality of nanoparticles;
   irradiating the plurality of nanoparticles with laser radiation from a laser;
   transferring thermal energy from the plurality of nanoparticles to the sample to heat the sample;
   wherein transferring thermal energy from the plurality of nanoparticles to the sample results in a phase change in the sample;
   exciting Raman scattering from the sample using the laser as the sample is heated to obtain a Raman spectrum associated with the sample as it is heated; and
   identifying the sample based on the Raman spectrum.

2. The method of claim 1 wherein placing the sample in proximity to the plurality of nanoparticles comprising providing physical contact between the sample and the plurality of nanoparticles.

3. The method of claim 1 wherein placing the sample in proximity to the plurality of nanoparticles comprises making physical contact between the sample and a thermal conductor and between the thermal conductor and the plurality of nanoparticles.

4. The method of claim 1 wherein the phase change comprises evaporation of the sample.

5. The method of claim 1 wherein the phase change comprises at least one of liquefaction or decomposition of the sample.

6. The method of claim 1 wherein transferring energy from the plurality of nanoparticles to the sample utilizes a plasmon resonance process.

7. The method of claim 1 wherein exciiting Raman scattering from the sample comprises using the laser source as the sample is heated further comprises obtaining a plurality of Raman spectra associated with the sample as a function of temperature, and wherein identifying the sample further comprises using the plurality of Raman spectra.

8. The method of claim 1 wherein identifying the sample based on the Raman spectrum comprises determining a sample temperature based, at least in part, on the Raman spectrum.

9. A method of characterizing a sample, the method comprising:
   placing the sample in contact with a plurality of nanoparticles;
   irradiating the plurality of nanoparticles with electromagnetic radiation at a first fluence, wherein the electromagnetic radiation includes ultraviolet, visible, infrared radiation, or any combination thereof;
   increasing a temperature of the plurality of nanoparticles from an influence of the electromagnetic radiation;
   transferring energy from the plurality of nanoparticles to the sample to heat the sample to a first temperature;
   collecting a first Raman spectrum from the sample at the first temperature;
   irradiating the plurality of nanoparticles with electromagnetic radiation at a second fluence greater than the first fluence;
   increasing the temperature of the plurality of nanoparticles from an influence of the electromagnetic radiation at the second fluence;
   transferring additional energy from the plurality of nanoparticles to the sample to heat the sample to a second temperature;

collecting a second Raman spectrum from the sample at the second temperature; and determining characteristics of the sample based on the first Raman spectrum and the second Raman spectrum.

10. The method of claim 9 wherein the first Raman spectrum is associated with a first phase of the sample and the second Raman spectrum is associated with a second phase of the sample.

11. The method of claim 10 further comprising associating a phase change temperature with the second phase of the sample.

12. The method of claim 9 wherein the second Raman spectrum is associated with at least one of evaporation, liquefaction, or decomposition of the sample.

13. The method of claim 9 wherein placing the sample in contact with the plurality of nanoparticles comprises:
providing a substrate;
providing a cover slip comprising the plurality of nanoparticles; and
positioning the sample between the substrate and the cover slip.

14. The method of claim 13 wherein the plurality of nanoparticles are disposed on a surface of the cover slip and the surface of the cover slip faces the sample.

15. The method of claim 9 wherein the electromagnetic radiation comprises laser radiation.

16. The method of claim 15 wherein irradiating the plurality of nanoparticles with lase radiation at a first fluence, collecting a first Raman spectrum from the sample, irradiating the plurality of nanoparticles with laser radiation at a second fluence, and collecting a second Raman spectrum from the sample are performed utilizing a same laser.

17. The method of claim 9 wherein the influence of the electromagnetic radiation comprises a plasmon resonance process.

18. A Raman microscopy system comprising:
a laser;
a cover slip including a layer of nanoparticles;
a sample region in the vicinity of the layer of nanoparticles and operable to receive a sample;
an optical system optically coupled to the laser, wherein the optical system is operable to:
direct the laser to impinge on the layer of nanoparticles and the sample, thereby transferring thermal energy from the layer of nanoparticles to the sample to heat the sample;
wherein transferring thermal energy from the plurality of nanoparticles to the sample results in a phase change in the sample; and
collect Raman spectra scattered from the heated sample as the laser impinges on the sample and as the sample is heated; and
a spectral detector optically coupled to the optical system and operable to receive the Raman spectra scattered from the sample.

19. The Raman microscopy system of claim 18 wherein the sample is in physical contact with the layer of nanoparticles.

20. The Raman microscopy system of claim 18 wherein the layer of nanoparticles is optically upstream of the sample region.

21. The Raman microscopy system of claim 18 wherein the optical system comprises a microscope objective.

* * * * *